(12) United States Patent
Vaidyanathan

(10) Patent No.: US 7,333,218 B2
(45) Date of Patent: *Feb. 19, 2008

(54) SYSTEMS AND METHODS FOR DETERMINING THE LOCATION AND ANGULAR ORIENTATION OF A HOLE WITH AN OBSTRUCTED OPENING RESIDING ON A SURFACE OF AN ARTICLE

(75) Inventor: Janakiraman Vaidyanathan, South Windsor, CT (US)

(73) Assignee: United Technologies Corporation, Hartford, CT (US)

( * ) Notice: Subject to any disclaimer, the term of this patent is extended or adjusted under 35 U.S.C. 154(b) by 286 days.

This patent is subject to a terminal disclaimer.

(21) Appl. No.: 11/170,045

(22) Filed: Jun. 28, 2005

(65) Prior Publication Data

US 2007/0019213 A1 Jan. 25, 2007

(51) Int. Cl.
*G01B 11/90* (2006.01)
(52) U.S. Cl. .................. 356/614; 356/608; 356/626; 382/152
(58) Field of Classification Search ........ 356/603–626; 250/330, 336.1; 382/141–154
See application file for complete search history.

(56) References Cited

U.S. PATENT DOCUMENTS

| | | | | |
|---|---|---|---|---|
| 4,647,208 A | * | 3/1987 | Bieman | 356/615 |
| 5,054,087 A | * | 10/1991 | Carbon et al. | 382/152 |
| 5,111,046 A | | 5/1992 | Bantel | 250/330 |
| 5,702,288 A | | 12/1997 | Liebke et al. | 451/36 |
| 5,773,790 A | * | 6/1998 | Moore et al. | 219/121.71 |
| 6,380,512 B1 | | 4/2002 | Emer | 219/121.71 |
| 6,866,200 B2 | * | 3/2005 | Marx et al. | 235/491 |
| 6,909,800 B2 | * | 6/2005 | Vaidyanathan | 382/152 |

* cited by examiner

*Primary Examiner*—Sang H. Nguyen
(74) *Attorney, Agent, or Firm*—Colin L. Cini

(57) ABSTRACT

Provided are systems 10 and methods 100 for determining both the location and angular orientation of holes 12 with openings 14 on a surface 16 of an article 18 that are at least partially obstructed. In a method of the present invention, a scanning system 10 that includes a laser spot projector 40, a laser spot sensor 42, a memory device 48 and a processor 50 is provided. A laser beam 44 is projected onto the surface 16 of the article 18 in a region 24 containing at least one hole 12 and the spot sensor receives light reflections 46. A series of points 52 representing the scanned region is stored as a point cloud 54 in the memory device 48. The point cloud 54 is then manipulated to calculate the location and angular orientation of each hole in the region in relation to one or more pre-existing, article datums 22.

7 Claims, 5 Drawing Sheets

SYSTEMS AND METHODS FOR DETERMINING THE LOCATION AND ANGULAR ORIENTATION OF A HOLE WITH AN OBSTRUCTED OPENING RESIDING ON A SURFACE OF AN ARTICLE

CROSS-REFERENCE TO RELATED APPLICATIONS

This application discloses subject matter related to copending U.S. patent application "THERMAL IMAGING AND LASER SCANNING SYSTEMS AND METHODS FOR DETERMINING THE LOCATION AND ANGULAR ORIENTATION OF A HOLE WITH AN OBSTRUCTED OPENING RESIDING ON A SURFACE OF AN ARTICLE." (APPLICANT REFERENCE NUMBER EH-11506), filed concurrently herewith.

BACKGROUND OF THE INVENTION (1) Field of the Invention

The invention relates to gas turbine engine components, and more particularly to systems and methods for determining the location and angular orientation of a hole containing an obstructed opening on a surface of such components.

(2) Description of the Related Art

Many internal components of gas turbine engines are exposed to gas temperatures that exceed their base material's melting temperature. For that reason, internal components such as turbine rotor blades, turbine stator vanes, combustor liners, shroud segments and the like must be thermally protected for improved durability. Typically, internal channels direct lower-temperature air inside these components to reduce their temperature. The lower-temperature air exits the components via a series of small holes, forming a protective film that surrounds the external surfaces of the components. These holes, typically called film-cooling holes, are sized, located and angularly oriented to apportion the lower-temperature air only where it is required. The surfaces are usually further protected with insulating, thermal barrier coatings (TBCs). Typical, state of the art coatings comprise a metallic bond layer and a ceramic top layer. Despite the use of film cooling and thermal barrier coating, some components deteriorate over time and must eventually be restored or replaced altogether. Typically, one or more approved repairs can restore a deteriorated component to a like-new condition at a fraction of the cost of a replacement component.

Conventional restoration of a deteriorated component begins with the removal of the thermal barrier coating by chemical and/or mechanical means. Once the coating is removed, the component is inspected for distress and scrapped if found unserviceable. If the distress is within serviceable limits, the areas of distress and the multitude of film cooling holes are filled using the TURBOFIX® diffusion brazing repair process available under license from the assignee of the present invention. The TURBOFIX® diffusion brazed surfaces are then abrasively blended before new coating is applied. Once the component is coated, each of the film cooling holes is re-drilled using a laser, abrasive water jet, or other suitable drilling means.

In some instances, a component may only require the removal of the coating and application of a new coating to restore the component to like-new condition. Unfortunately, the application of the new coating partially or wholly obstructs the openings of the original film cooling holes. Even the slightest obstruction can negatively affect the film cooling of the component surfaces. In these instances, if it were possible to precisely determine the location and angular orientation of the film cooling holes even though they are partially or wholly obstructed with coating, then the coating could be reamed from the openings using a laser, abrasive water jet or other suitable drilling means. The application of new coating and reaming of the film cooling holes eliminates the time-consuming TURBOFIX® diffusion brazing repair steps. Any reduction in component restoration time or cost significantly benefits a gas turbine engine operator.

There are many challenges involved with determining the location and angular orientation of film cooling holes with obstructed openings. First, the hole diameters are very small, typically less than 0.020 inch. Second, the hole openings are at least partially obstructed with a coating having a thickness of between 0.002-0.020 inch. Third, the hole openings are located on complex, three-dimensional surfaces that may vary slightly from component to component and with extended operation at high temperatures.

One method of determining the locations of film cooling holes uses a manual vision system. According to this method, the locations of the holes are manually located by viewing each hole through a vision system camera that projects a magnified two-dimensional image of the hole opening on a video monitor. This method is labor intensive and since the operator only views a two-dimensional projection from the top of the holes, the hole's angular orientation is not accurately determined.

Another method of inspecting the location of film cooling holes uses an illumination system. According to this method, an array of holes is illuminated from within an internal cavity. An external video camera collects luminance data for display on a monitor and comparison to a reference luminance. This inspection method is useful for determining if a proper size hole is present, but does not verify the exact location and angular orientation of the holes. Also, the method is inoperable for holes that are partially or wholly obstructed with a coating.

Yet another method of inspecting film cooling holes uses an infrared radiometer system. According to this method, hot and cold air is alternately directed into hollow channels within a component and allowed to exit the cooling holes. An imaging infrared radiometer generates a series of images during the heat-up and cool-down cycles. This method is useful for inspecting for the existence of the holes, but does not verify their exact location and angular orientation.

What is therefore needed is an automated system and method for determining the location and angular orientation of holes with openings on surfaces that are at least partially obstructed with a thermal barrier coating.

BRIEF SUMMARY OF THE INVENTION

Provided are systems and methods for determining both the location and angular orientation of holes with openings on a surface of an article that are at least partially obstructed. In a method of the present invention, a scanning system including a laser spot projector, a laser spot sensor, a memory device and a processor are provided. A laser beam is projected onto the surface of the article in a region containing a hole and the spot sensor receives light reflections. A series of digital coordinate points representing the scanned region is stored as a point cloud in the memory device. The point cloud is then manipulated to calculate the location and angular orientation of each hole in the region in relation to one or more pre-existing, article datums.

BRIEF DESCRIPTION OF THE SEVERAL VIEWS OF THE DRAWINGS

When referring to the above listed drawings, like reference numerals designate identical or corresponding elements throughout the various views.

DETAILED DESCRIPTION OF THE INVENTION

Figure 1:
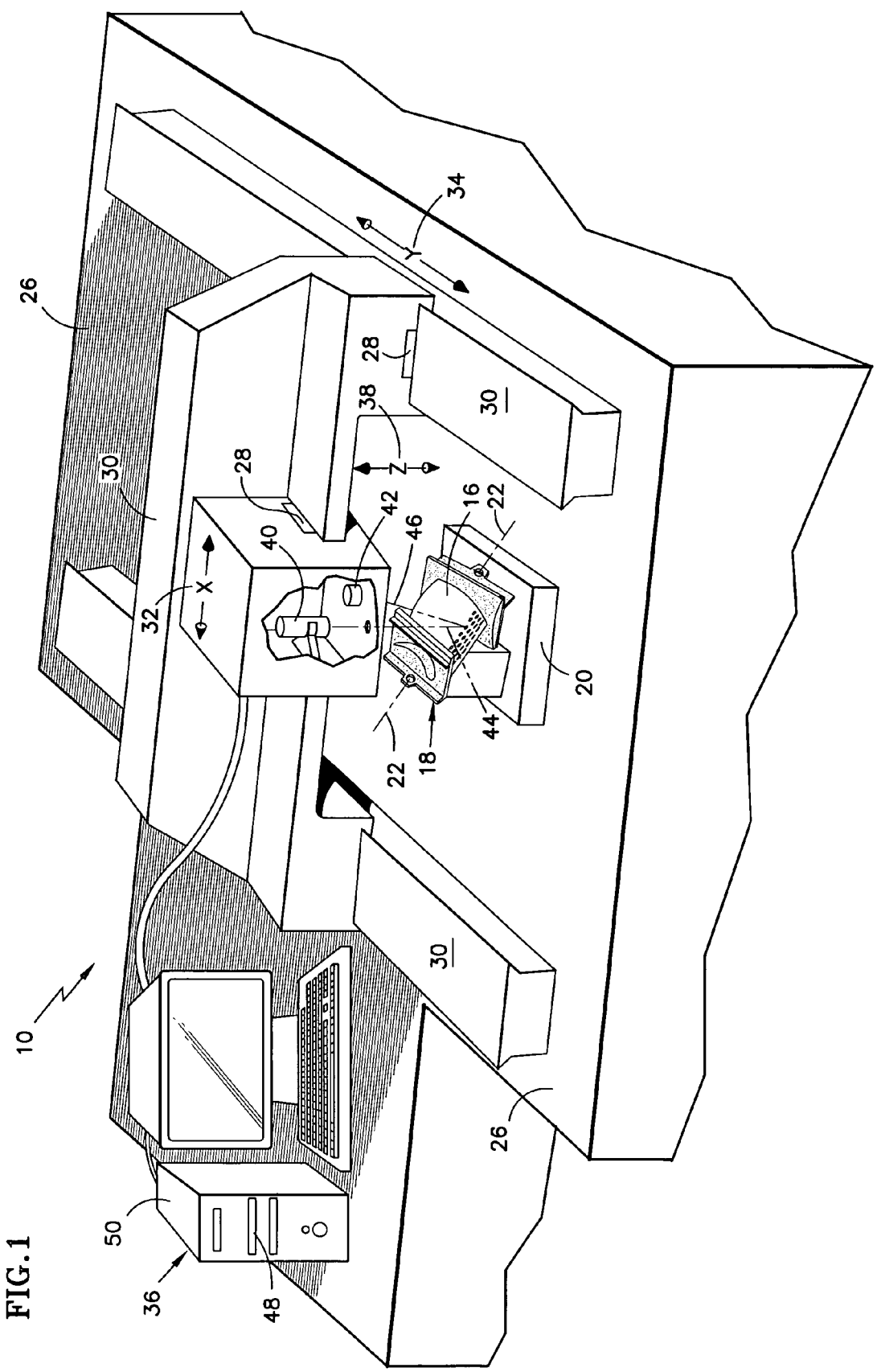
FIG. 1 is a simplified perspective view of a laser scanning system in accordance with an embodiment of the present invention.
Figure 2:
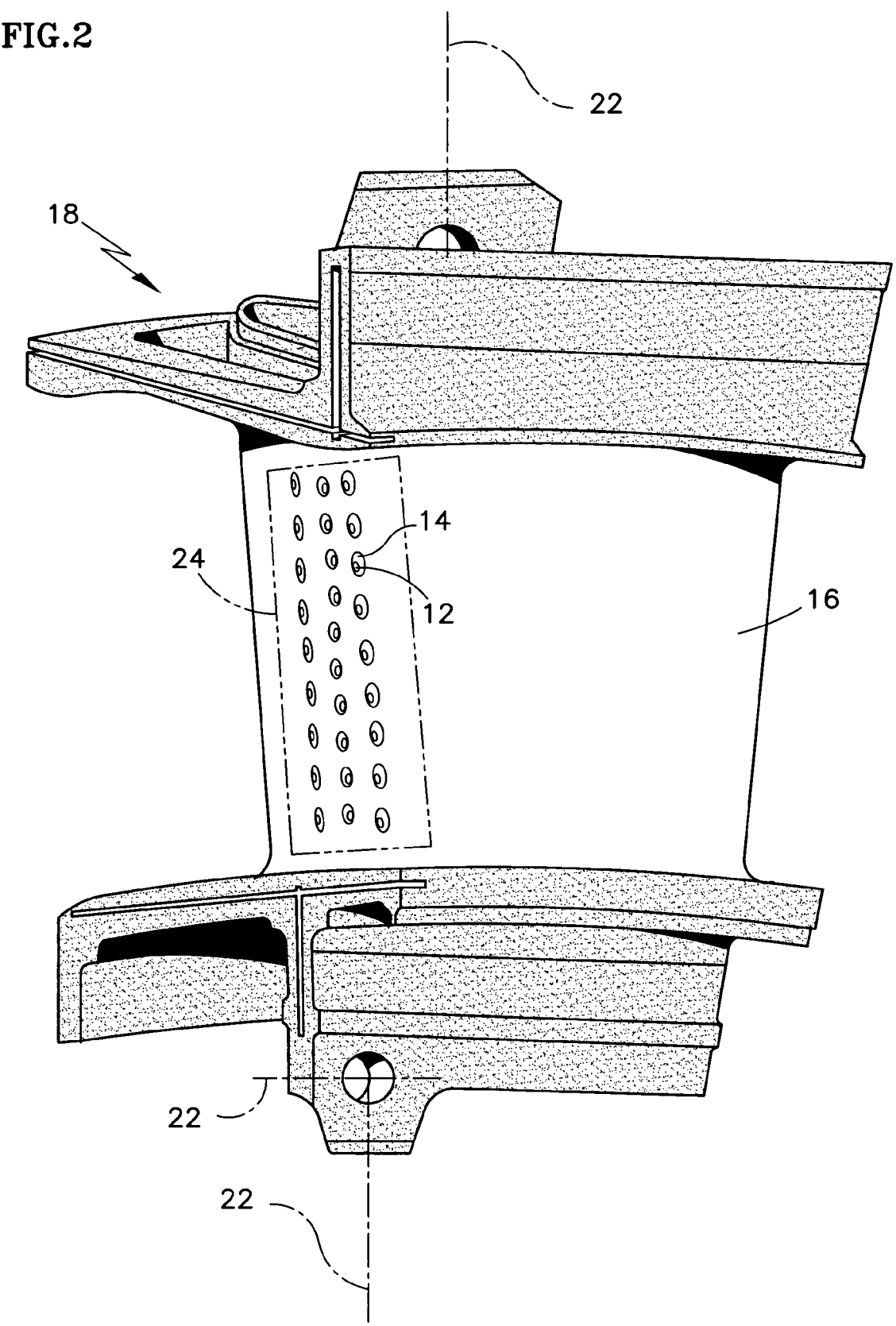
FIG. 2 is a perspective view of a gas turbine vane, illustrating a region containing several holes with various levels of thermal barrier coating obstruction.

As illustrated in FIG. 1, a laser scanning system 10 according to an embodiment of the present invention is used to determine the location and angular orientation of one or more holes 12 with obstructed openings 14 on a surface 16 of a typical article 18 as illustrated in FIG. 2. In the example shown, the article 18 is a vane for use inside a gas turbine engine. A stationary fixture 20 accurately establishes the location of the article 18 according to one or more preexisting article datums 22. A region 24 of the surface 16 containing the holes 12 and openings 14 is oriented for maximum exposure to the system 10. The use of an accurate fixture 20 is extremely important, since the resulting hole 12 locations and angular orientations are calculated and stored in relation to the one or more datums 22.

A multi-axis controller 26, commonly used throughout industry for accurate positioning during machining, measurement and other operations, carries the fixture 20 and article 18. The controller 26 comprises a servo 28 for driving a cross-slide 30 linearly about each of an X-axis 32 and a Y-axis 34 according to instructions from a computer 36. Since the cross-slides 30 move linearly within an X-Y plane only, movement within a Z-axis 38 is constant. The controller 26 provides access to surfaces 16, without having to remove the article 18 from the fixture 20.

A laser spot projector 40 and a laser spot sensor 42 are mounted proximate to one another on one of the cross-slides 30. A small diameter laser beam 44, typically fifty micrometer or less, is directed from the spot projector 40 toward the surface 16 and the sensor 42 receives a reflected light 46 back from the surface 16. By measuring where the reflected light 46 contacts the sensor 42, the Z-axis 38 distance from the surface 16 to the projector 40 may be calculated through triangulation. The z-axis 38 distance varies in response to changes in the topology of the surface 16. A Keyence, LV series laser spot projector 40 and spot sensor 42 were used in the exemplary system 10.

The computer 36 comprises a memory device 48 and a processor 50 and is connected to the controller 26 via cables. The computer 36 instructs the controller 26 to position the cross-slides 30 about the X-Y plane by means of the servos 28. Since the projector 40 and sensor 42 are mounted to one of the cross-slides 30, the laser beam 44 scans the surface 16 as the cross-slides 30 traverse the article 18. A scan line density, or distance between constant X-axis 32 and Y-axis 34 scan positions (or scan lines), may be increased or decreased to produce a desired surface 16 resolution. The processor 50 is programmed using C++ or any other suitable programming language.

While scanning the surface 16, the sensor 42 outputs a calibrated Z-axis distance as an analog voltage to the memory device 48. The corresponding, instantaneous X-axis 32 and Y-axis 34 distances are generated from the servos 28 driving the cross-slides 30. These three data sources: the X-axis 32 and Y-axis 34 distances from the servos 28 and the Z-axis 38 distance calibrated from the spot sensor 42, are captured continuously using a high-speed PC data bus and are stored in the memory device 48 as a series of points 52.

Figure 3:
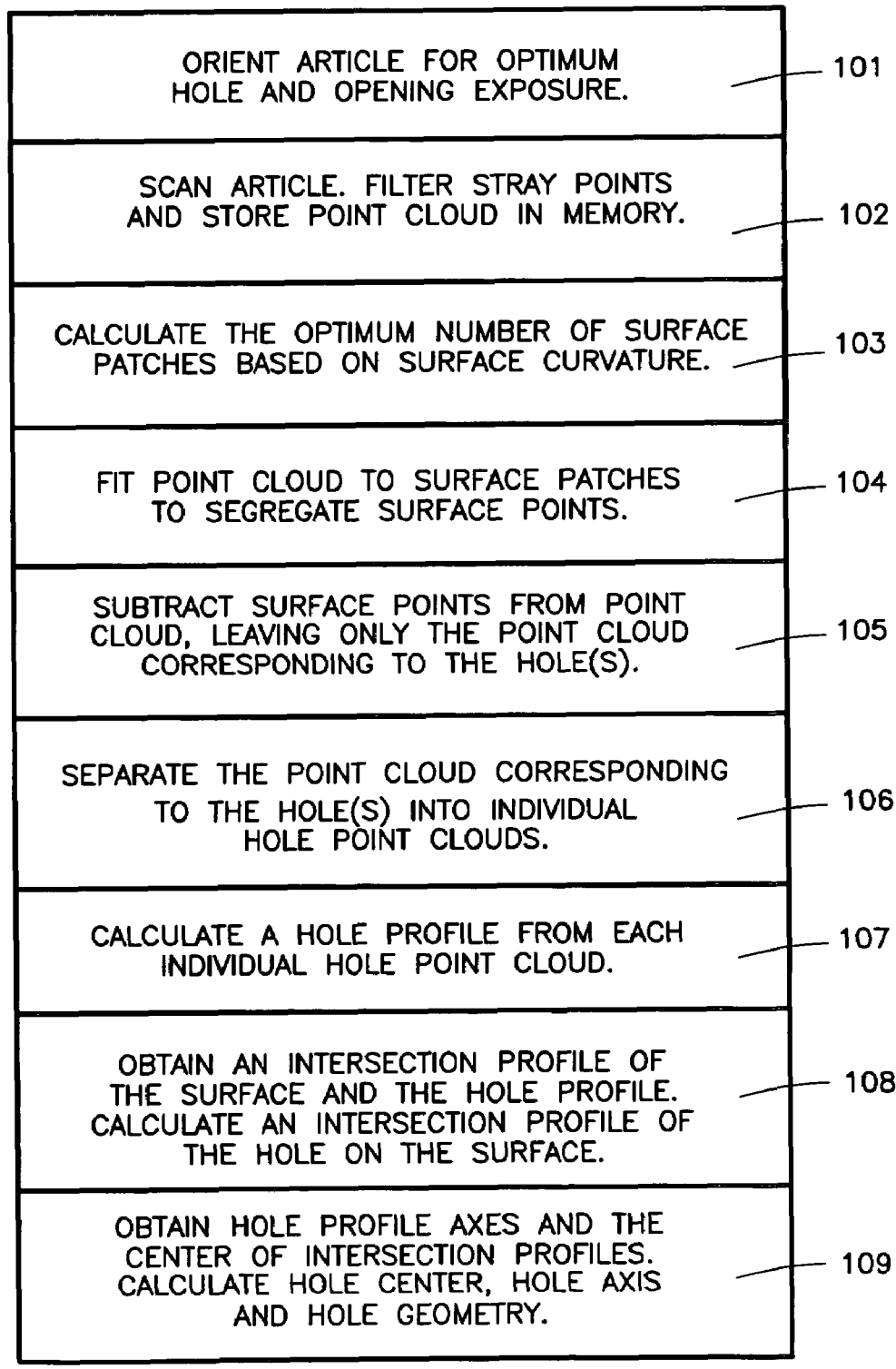
FIG. 3 is a schematic diagram detailing various steps according to a method of the present inventive.

Accordingly, FIG. 3 illustrates a series of method steps 100 for determining the location and angular orientation of one or more holes 12 with at least partially obstructed openings 14 on a surface 16 using system 10.

Referring first to step 101 of the method, the article 18 is oriented so the maximum number of holes 12 and openings 14 are exposed for scanning by the system 10. It is important that a maximum hole 12 to surface 16 intersection area is exposed to the system 10 to ensure all the holes 12 and openings 14 are captured during scanning. The optimal orientation may be determined through experimentation or from a Computer Aided Design (CAD) file of the article 18 if one exists.

Figure 4:
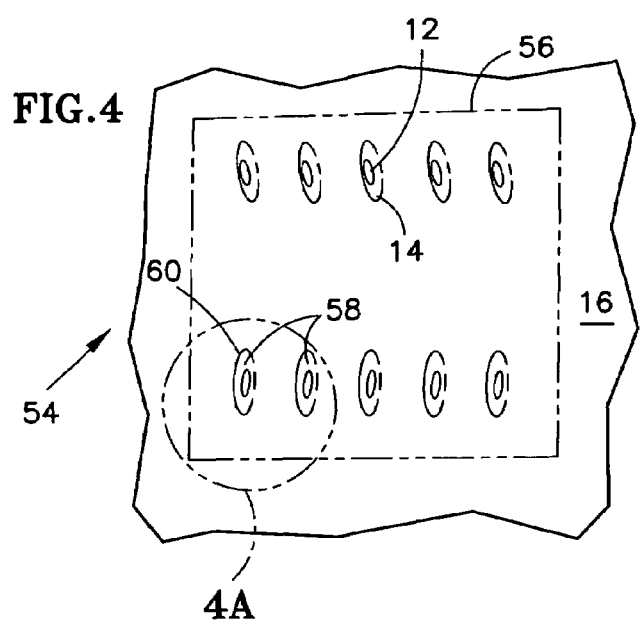
FIG. 4 is a partial perspective schematic view of a point cloud scan of a portion of the region of FIG. 2.
Figure 4A:
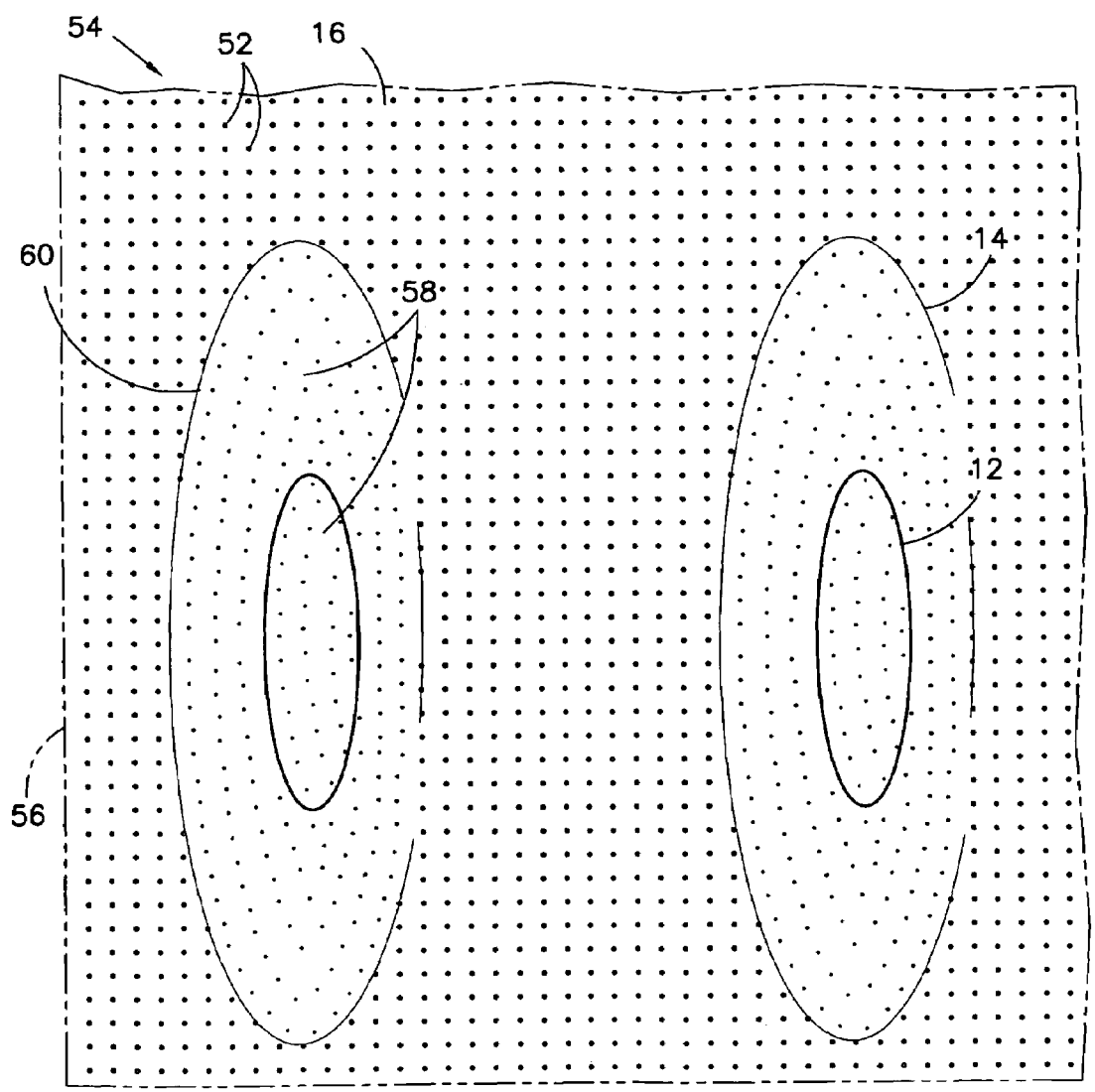
FIG. 4a is a close up, partial perspective view of the point cloud scan of FIG. 4.

Referring now to step 102 of FIG. 3 and examples of FIGS. 4 and 4a, the topography of the exposed surface 16 is scanned into many individual digital coordinate points 52, known as a point cloud 54, using the system 10 as earlier described. The point cloud 54 is filtered to remove all outlying and extraneous points created by stray laser beam 44 reflections and system 10 noise. The point cloud 54 is stored in the memory device 48 for further manipulation by the processor 50.

Manipulation of the point cloud 54 begins in step 103 of FIG. 3 by calculating an optimum number of surface patches 56 to split the point cloud 54 into. The calculation of the optimum number of surface patches 56 is based on the scan line density, resolution desired in the hole region 24 and the computation time allowed. Surfaces 16 with extreme curvature will have the point cloud 54 separated into more surface patches 56 than surfaces 16 with minimal curvature. The importance of this step will become apparent, as the remaining method steps are detailed below.

The points 52 within each surface patch 56 are individually analyzed, in step 104 of FIG. 3, to determine which points 52 represent the surface 16. If the points 52 making up the surface 16 are closer than a specified distance away from all neighboring points 52, then they belong to the surface 16. The specified distance is based upon the surface 16 curvature and scan line density. Points 52 representing the surface 16 follow a predictable pattern and are nearly uniform in distance away from any other surface points 56. This step is important, because a point 52 belonging to a hole 12 or opening 14 will be located a greater distance away from any point 52 residing on the surface 16. The points 52 representing the holes 12 or openings 14 do not belong to a surface 16 and therefore, are easily identified and removed from the surface 16.

With the surface patches 56 now containing only those points 52 that represent the surface 16, the points 52 representing the holes 12 and openings 14 are isolated into a single group in step 105 of FIG. 3. The points 52 that represent the surface 16 are digitally subtracted from the point cloud 54 to reveal a hole cloud 58 (FIGS. 4 and 4a) representing only the holes 12 and openings 14 but not the surface 16. The hole cloud 58 is further separated into individual hole clouds 60 based on the nominal, X-axis 32 and Y-axis 34 distances between holes 12 in step 106 of FIG. 3. In practice, the separation of the hole cloud 58 into individual hole clouds 60 happens easily given the distance between holes.

With each hole 12 and opening 14 now defined by an individual hole cloud 60, hole profiles 62 (FIG. 5) are calculated in step 107 of FIG. 3. Typically, the thermal barrier coating only obstructs portions of the openings 14, so points 52 representing the inside of the holes 12 are available for manipulation. For any conic shape such as a cone or a cylinder, only a minimum number of points 52 are required to define the full geometry. If many points 52 are available in the individual hole clouds 60, which is generally the case, then a best fitting algorithm may be used to calculate an even more accurate hole 12 geometry. For other, shaped-hole 12 geometries (not shown), the individual hole clouds 60 are compared with corresponding template geometries and hole profiles 62 are created using a best fit algorithm.

Now that the hole profiles 62 exist, intersection profiles 64 of the openings 14 on the surface 16 are calculated in step 108 of FIG. 3. Points 52 from each of the hole profiles 62 and the surface 16 are compared and the closest points 52 representing the surface 16 are extracted. From the extracted points 52, intersection profiles 64, representing the intersection of the openings 14 and the surface 16 are created.

Figure 5:
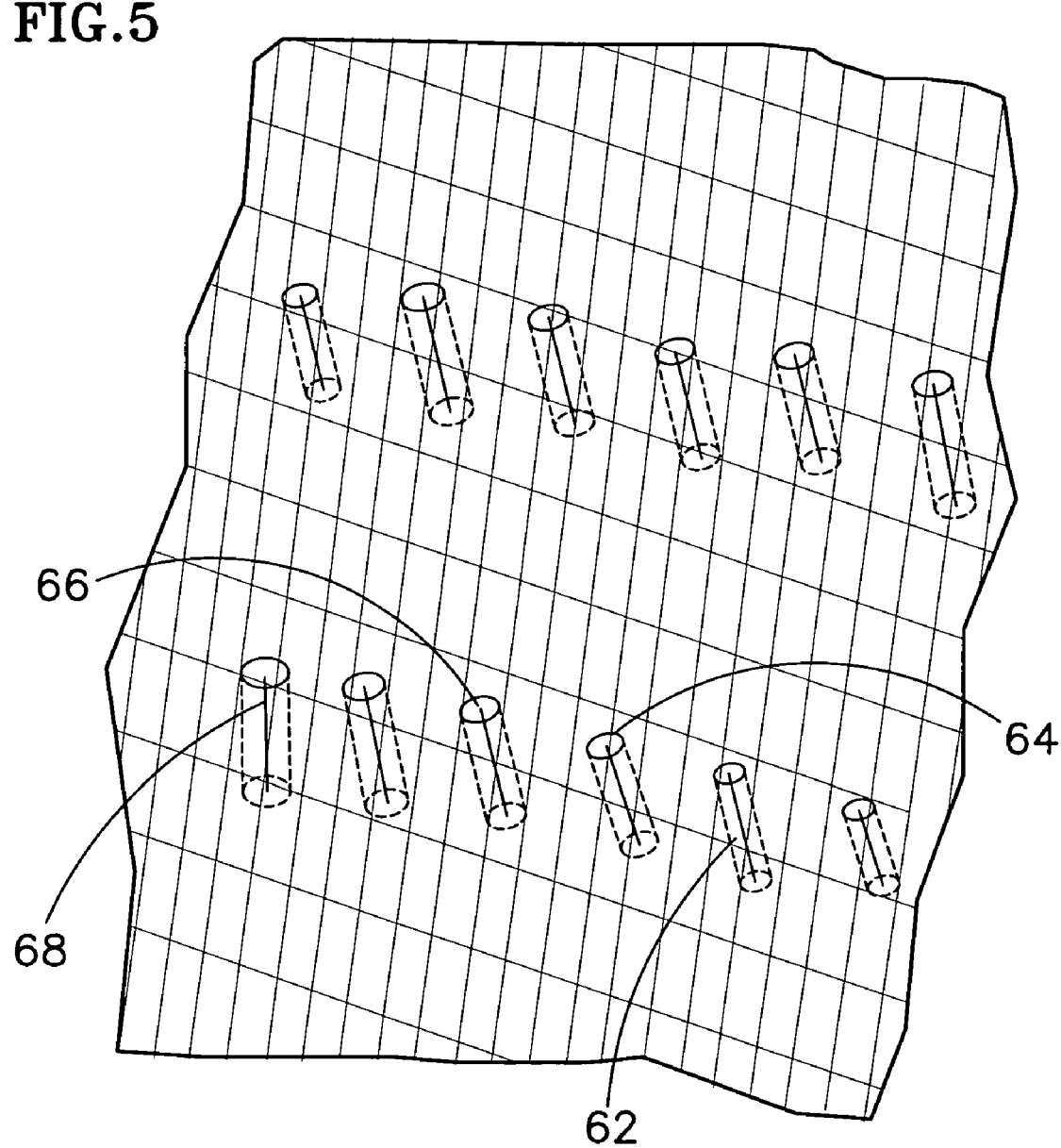
FIG. 5 is a partial perspective view showing the location and angular orientation of the holes of the portion of the region of FIG. 2.

From the hole profiles 62 and intersection profiles 64, representations of the actual holes 12 are created in step 109 of FIG. 3. Round holes 12 are represented as cylinders terminating at the surface 16. An example is best illustrated in FIG. 5. The hole centers 66, hole axes 68 and the hole profiles 62 are stored in the memory device 48 for later use by a laser, abrasive water jet or other suitable reaming device.

Since the hole centers 66, hole axes 68 and the hole profiles 62 are calculated and stored in relation to the one or more preexisting datums 22, it is important that the reaming device account for this. A similar fixture 20 that correlates the datums 22 with the reaming device's coordinate system must therefore be used.

While embodiments of an inventive system and method have been described in the context of obstructed film cooling holes in turbine components, it is to be understood that other articles with obstructed holes would similarly benefit. For example, a perforated article that has been painted after the perforations are formed would benefit. Accordingly, the present invention is intended to embrace those alternatives, modifications and variations as fall within the broad scope of the appended claims.

What is claimed is:

1. A method of determining a location and an angular orientation of one or more holes with obstructed openings that reside on a surface of an article and includes at least one datum, comprising the steps of:

providing a scanning system including a multi-axis controller, a laser spot projector, a laser spot sensor, a memory device and a processor;

scanning a region of the surface containing the one or more holes by projecting a laser beam from the laser spot projector and receiving laser light reflections with the spot sensor while moving said projector and said sensor in relation to the article with said controller;

storing digital points in said memory device as a point cloud representing the scanned region measured in relation to the at least one datum; and manipulating the point cloud with said processor by filtering the point cloud to remove points that are beyond a predetermined distance away from any other point in the point cloud, leaving a point cloud representing the surface to determine the location and angular orientation of the one or more holes in relation to the at least one datum.

2. The method of claim 1 wherein the manipulating step further comprises subtracting the point cloud representing the surface from the point cloud representing the scanned region to isolate a point cloud representing the one or more holes.

3. The method of claim 2 wherein the manipulating step further comprises isolating one or more individual point clouds, each representing a single hole from the point cloud representing the one or more holes.

4. The method of claim 3 wherein the manipulating step further comprises creating a hole profile from each of the individual point clouds.

5. The method of claim 4 wherein the manipulating step further comprises extracting points from both the point cloud representing the surface and the individual hole profiles and creating an intersection profile representing an opening for each hole.

6. The method of claim 5 wherein the manipulating step further comprises calculating a hole center and a hole profile axis from the intersection profile to create a hole form for each hole.

7. The method of claim 6 wherein the manipulating step further comprises calculating and storing in the memory device a location and angular orientation of each hole from the hole forms and in relation to the at least one datum.

* * * * *